(12) United States Patent
Matheny

(10) Patent No.: US 10,512,711 B2
(45) Date of Patent: *Dec. 24, 2019

(54) ARTICLES FOR TISSUE REGENERATION WITH BIODEGRADABLE POLYMER

(71) Applicant: CorMatrix Cardiovascular, Inc., Roswell, GA (US)

(72) Inventor: Robert G Matheny, Norcross, GA (US)

(73) Assignee: CORMATRIX CARDIOVASCULAR, INC, Roswell, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,188

(22) Filed: Apr. 9, 2015

(65) Prior Publication Data

US 2015/0209478 A1 Jul. 30, 2015

Related U.S. Application Data

(63) Continuation of application No. 11/747,028, filed on May 10, 2007, now Pat. No. 9,034,367.

(51) Int. Cl.
| | |
|---|---|
| *A61L 27/54* | (2006.01) |
| *A61L 27/14* | (2006.01) |
| *A61L 27/36* | (2006.01) |
| *A61L 27/58* | (2006.01) |
| *A61K 38/00* | (2006.01) |

(52) U.S. Cl.
CPC ............. *A61L 27/54* (2013.01); *A61L 27/14* (2013.01); *A61L 27/3604* (2013.01); *A61L 27/3629* (2013.01); *A61L 27/3633* (2013.01); *A61L 27/3641* (2013.01); *A61L 27/58* (2013.01); *A61K 38/00* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 7,914,808 B2 | 3/2011 | Malaviya et al. | |
| 8,758,448 B2* | 6/2014 | Matheny | A61K 35/12 623/23.72 |
| 9,034,367 B2* | 5/2015 | Matheny | A61L 27/14 424/443 |
| 9,277,999 B2* | 3/2016 | Badylak | A61L 27/14 |
| 9,295,757 B2* | 3/2016 | Patel | A61L 27/3633 |

(Continued)

OTHER PUBLICATIONS

Chu C, "Textile Based Biomaterials for Surgical Applications". Polymer Biomaterials. Dumitriu (Ed). New York: Marcel Dekker Inc, 2002. p. 491-501.*

*Primary Examiner* — Allison M Fox
(74) *Attorney, Agent, or Firm* — Francis Law Group

(57) ABSTRACT

The invention is to articles made from extracellular matrix sheets that encase biodegradable polymeric material. Methods of healing wounds or regenerating tissue at sites of defect by placing said articles in mammals are claimed. The biodegradable polymer can change quality upon contact with a physiological parameter such as temperature or pH that causes, for example, a liquid polymer to gel or harden. The degradation of the polymer can be controlled to suit a tissue regeneration or wound healing time course. Additional components such as proteins, cells and drugs can be added to the biopolymer composition.

2 Claims, 1 Drawing Sheet

(56) References Cited

U.S. PATENT DOCUMENTS

| | | | |
|---|---|---|---|
| 2003/0023316 A1* | 1/2003 | Brown | A61F 2/0063 623/23.72 |
| 2005/0260612 A1* | 11/2005 | Padmini | A61F 2/08 435/6.14 |
| 2006/0147433 A1* | 7/2006 | Hiles | A61K 35/37 424/93.7 |
| 2007/0026053 A1* | 2/2007 | Pedrozo | A61F 2/30756 424/443 |

* cited by examiner

ARTICLES FOR TISSUE REGENERATION WITH BIODEGRADABLE POLYMER

CROSS-REFERENCES TO RELATED APPLICATIONS

This application is a continuation of U.S. application Ser. No. 11/747,028, filed on May 10, 2007.

FIELD OF THE INVENTION

The invention relates to articles made with extracellular matrix materials.

BACKGROUND OF THE INVENTION

Tissue regeneration has been accomplished by using extracellular matrix material derived from mammalian tissues. Some of these mammalian tissues that have been described in patent literature include small intestine submucosa (SIS), liver basement membrane (LBM), urinary bladder submucosa (UBS) and stomach submucosa (SS). See U.S. Pat. Nos. 5,554,389, 4,902,508, and 5,281,422. Enamel matrices, which are the extracellular matrix around forming teeth, are described in U.S. Pat. No. 7,033,611. Extracellular matrices from these tissues have been isolated and described as solid materials (sheets and particulates), and in fluidized or emulsion forms made by reconstituting particulate in a suitable buffer. Presently, these extracellular matrix compositions are used for tissue grafting, wound healing, and tissue regeneration purposes.

It would be advantageous to the field of tissue engineering to invent articles and compositions for effecting improved tissue regeneration.

SUMMARY OF THE INVENTION

The invention is an article comprising a sheet of extracellular matrix encasing a composition comprising a biodegradable polymer.

The invention is also an article comprising a conduit formed of an outer tube and a concentric inner tube, each tube comprising extracellular matrix sheets, said conduit having a space between said outer tube and said inner tube, said space occupied with a composition comprising a biodegradable polymer.

The invention is further a method comprising identifying a defect or wound in tissue in a mammal, providing an article comprising a sheet of extracellular matrix encasing a composition comprising a biodegradable polymer, contacting said defect or wound with said article, and regenerating tissue at said defect or healing said wound, whereby said composition biodegrades in said mammal at a designed rate.

These and other elements of the invention are detailed below.

DETAILED DESCRIPTION OF THE INVENTION

Figure 1A:
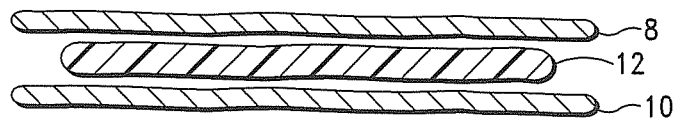
FIG. 1A depicts an article having two sheets of extracellular matrix encasing a composition comprising biodegradable polymer.

The invention is an article made of one or more extracellular matrix sheets encasing a composition comprising a biodegradable polymer. The article can comprise two or more sheets of extracellular matrix. Two sheets can sandwich an amount of the composition comprising a biodegradable polymer. The invention is also an article comprising concentric tubes of extracellular matrix forming a conduit with a space between the tubes that is filled with a biodegradable polymer.

The article of concentric tubes is useful for tissue regeneration or wound healing at a vessel in the body. The vessel can be for example a blood vessel, such as an artery or vein. The vessel can also be a large intestine, or small intestine. The vessel can also be any number of tubes that connect to and from the organs in the body, for example, in the reproductive organs (e.g. fallopian tubes, prostate), bladder, urinary tract, gastrointestinal tract, lung, heart and kidney vessels, and in general any tubular part of the mammalian body in need of repair. The sizes and design of the article will be adjusted for the location that the article is being placed in the body, thus, for example, a large intestine will receive a large conduit, and an artery or vein a much smaller one.

The inventions are useful for placing in a mammal in need of tissue regeneration to effect tissue regeneration at the site of placement of the article or device. The extracellular matrices used in the article (i.e. the sheets of extracellular matrix) can be from one or more than one source of extracellular matrix in a mammal, for example one sheet can be SIS and one sheet can be SS, or both sheets (or tubes) can be SIS.

The biodegradable composition can change consistency in response to a physiological condition. Thus, the composition outside the body can be a certain consistency (for example a liquid) and then when placed in the body the consistency can change in response to the change in pH, temperature, or enzymatic activity present in the body at the site of placement of the article. Accordingly, and optimally, the composition might be a liquid before placement in the body and gel upon contact with the environment in the body with the physiological condition that makes the composition gel (e.g. pH difference, temperature difference, or enzymatic activity).

The biodegradable polymer composition can comprise an additional element, for example a protein, a cell, or a drug.

The article that is a conduit can be formed of an outer tube and a concentric inner tube. Each tube can comprise extracellular matrix sheets, and the conduit can have a space between the outer tube and the inner tube. The space is occupied with a composition comprising a biodegradable polymer. As with the other articles of the invention, the composition between the two pieces of extracellular matrix can also comprise an additional component, such as a protein, a cell, or a drug.

The composition can also change consistency in response to a physiological condition, as described earlier.

The biodegradable polymer composition in all these articles can be designed to degrade at a predetermined or designed rate. For example, if it is determined that the extracellular matrix sheets that encase the biodegradable polymer need about 3 months of support before they have more or less fully assimilated as new tissue at the site, then the biodegradable polymer should be designed to be fully degraded by 3 months of presence in the body. The polymer composition can be adjusted to degrade at different rates depending on the polymer composition and its known rate of degradation in the body, as well as by manipulating other factors such as the specific composition of the polymer, the quantity of polymer placed in the article, as well as by manipulating other parameters in the composition.

The invention is also a method of using the articles of the invention. The articles can be used to generate new tissue at a site of defect, or to heal a wound in the tissue. Most commonly humans are the subjects for this treatment, but any mammal can be treated using these methods. Mammals such as horses, dogs, cats and other mammals (particularly domesticated mammals) in need of tissue regeneration can be treated with these methods.

The method includes that a defect or wound in mammalian tissue is identified in a subject mammal. An article such as described above having extracellular matrix encasing a composition comprising a biodegradable polymer is provided. The defect or wound in the subject mammal is treated by contacting the defect or wound with the article. The articles can be either a flat sandwich type configuration, encasing the composition, or a conduit of two concentric tubes of extracellular matrix that encase the composition between the concentric tubes, or the article can be some other shape suitable to the purpose of tissue regeneration or wound healing at the site. As a result of placing the article at the site in the mammal, tissue is regenerated at the defect or the wound is healed, about which time the biodegradable polymer in the composition has degraded or nearly degraded.

The tissue to be repaired using the articles of the invention, and the methods of the invention include myocardial tissue, pancreatic tissue, and liver tissue, for example.

As with the articles of the invention, the method invention provides that the composition can also include an additional component, such as a protein, cell or drug.

The article of the invention is made up of a composition comprising a biodegradable polymer. The biodegradable polymer provides support for the extracellular matrix components of the articles and then slowly degrades as the matrix integrates into the surrounding tissue and becomes new tissue in the animal.

Biodegradable polymers can be either natural or synthetic. A material is called degradable with respect to specific environmental conditions if it undergoes a degradation to a specific extent within a given time measured by specific standard test methods. Degradation is also an irreversible process leading to a significant change of structure of a material, typically characterized by a loss of properties (e.g. integrity, molecular weight, structure or mechanical strength) and/or fragmentation. Degradation is affected by environmental conditions and proceeds over a period of time comprising one or more steps. Disintegration is the falling apart into very small fragments of packaging or packaging material caused by degradation mechanism. The general criteria for selecting a polymer for use as a biomaterial is to match the mechanical properties and the time of degradation to the needs of the application. The ideal polymer for a particular application would be configured so that it has mechanical properties that match the application, remaining sufficiently strong until the surrounding tissue has healed; does not invoke an inflammatory or toxic response; is metabolized in the body after fulfilling its purpose, leaving no trace; is easily processable into the final product form; demonstrates acceptable shelf life and is easily sterilized. Some polymers suitable for use in the articles and devices of the invention include (but are not limited to) the following: polyglycolide (PGA), polylactide (PLA), poly .epsilon.-caprolactone, poly dioxanone (a polyether-ester), poly lactide-co-glycolide, polyamide esters, polyalkalene esters, polyvinyl esters, polyvinyl alcohol, polyanhydrides, and in addition to other polymers under investigation for similar applications. Natural polymers that might be used include (but are not limited to) polysaccharides (e.g. starch and cellulose), proteins (e.g. gelatin, casein, silk, wool), polyesters (e.g. polyhydroxyalkanoates), and others (e.g. lignans, shellac, natural rubber). This list is not intended to be exhaustive of all the biodegradable polymers suitable for use in the compositions.

The encasing of the biodegradable polymer composition can be accomplished by laminating the ends of the sheets to enclose the composition inside. The composition can be sandwiched between two sheets of extracellular matrix with the edges of the sheets laminated together, or somehow made to close either fully or partially to encase the composition inside. The article can also be made by providing a composition that is enclosed by a single sheet that folds over on itself to hold the composition. The three sides of the sheet can be laminated to itself to form an article that encases the composition and which is folded on one edge.

The sheets can be from the same source of extracellular matrix, i.e. both or all sheets can be made of SIS from a pig. The sheets can also be from different sources of extracellular matrix, for example the first sheet is SIS, and the second sheet is SS. Both the SIS and SS can be from the same species of mammal (pig) or each from a different species of mammal (SIS from pig, and SS from cow). Accordingly, such extracellular matrices as LBM and UBS can be used for making the sheets, and mixed and matched according to the needs of the animal being treated. For example, it may be beneficial to have an underside sheet of a higher tensile strength material such as SIS, and a topside sheet of a weaker strength such as LBM. Likewise with the concentric tubes the outer tube can be of SIS and the inner tube can be of LBM or UBS, the inner tubes providing less tensile strength but equal or greater tissue regenerative potential than the outer tube of SIS.

The sheets can be laminated to each other at the edges around an amount of composition comprising the biodegradable polymer that then becomes encased in the two sheets upon lamination of the outer sheets to each other. The lamination of the two outer sheets together can be partial or complete, so that the composition inside can be entirely contained within the two sheets, or can be permitted to ooze out from between the sheets upon placement in the subject receiving treatment. The two sheets may also be attached to each other by quilting of the sheets in the middle of the sheets much like a quilt is assembled when made of 2 or more layers of fabric.

The composition can be a mixture of more than one biodegradable polymer. Accordingly, in between the sheets of matrix can be of mixed source of biodegradable polymer, so that for example a biodegradable polymer composition can be a 50:50 mixture of PGA and PGLA, or some other permutations of mixtures that will serve the purpose of the composition in the article. The biodegradable polymer can also be mixed with a certain percentage of liquid, gel or particulate extracellular matrix. The function of the composition will be to support the extracellular matrix sheets or tubes until they have assimilated into new tissue in the animal, and thus the strength of the composition and the rate of its degradation in the animal will be two of the important parameters to adjust as the composition is fine-tuned for a particular specific application in a particular subject being treated.

Mammalian tissue sources are in general any tissue having an extracellular matrix that can be isolated from a mammal and de-cellularized. Thus for example, most mammalian organs are tissue sources. The tissue sources can be for example any mammalian tissue, including but not limited to the small intestine, large intestine, stomach, lung, liver, kidney, pancreas, placenta, heart, bladder, prostate, tissue surrounding growing tooth enamel, tissue surrounding growing bone, and any fetal tissue from any mammalian organ.

The mammal from which the extracellular matrix sheets are derived can be any mammal, including (but not limited to): humans, cows, pigs, dogs, cats, horses, rodents or any other mammal who provides the necessary material. Any mammal can potentially contribute extracellular matrix for making the sheets of the invention.

The forms of the extracellular matrices that make up the articles are generally forms such as sheets that can be folded or manipulated to both encase the biodegradable polymer, and form the desired shape for the article or device. Thus the articles or devices can form sandwiches, or conduits, or other shapes such a triangular shapes, circular shapes, irregular shapes, and shapes tailored or designed to fit specific locations in the animal.

The sheets in the article can have any number of shapes, e.g. square, rectangular, triangular, circular, or an irregular shape. The shape of the article can be tailored to fit the site where the article will be introduced into the body. Accordingly, the compositions that make up the center or encased portion of the article can be any of these forms, encased in one or more sheets of extracellular matrix. The form can also be a conduit having two concentric tubes with the space between the tubes filled with the biodegradable polymer composition. (see FIG. 1C)

The biodegradable polymer is useful to the articles and devices of the invention because it will hold a shape and retain a presence for a temporary period of time. As the sheet of extracellular matrix form new tissue, the biopolymer will help the sheets maintain a position or shape necessary until the tissue is formed. Ideally the degradation of the biopolymer is designed to match the needs of the application so that the biopolymer degrades as the new tissue is being formed, and eventually is completely gone by the time the new tissue is strong enough to fully support its new application in the body.

Extracellular matrix sheets and any incidental emulsion used in the composition filler can be obtained from the tissues of mammals by processes such as described in U.S. Pat. Nos. 5,554,389, 4,902,508, and 5,281,422. For example, the urinary bladder submucosa is an extracellular matrix that has the tunica mucosa (which includes the transitional epithelial layer and the tunica propria), a submucosal layer, 3 layers of muscularis, and the adventitia (a loose connective tissue layer). This general configuration is true also for small intestine submucosa (SIS) and stomach submucosa (SS). Obtaining enamel matrices is described in U.S. Pat. No. 7,033,611. Enamel matrix is extracellular matrix existing near forming teeth.

Matrices can be used in whole or in part, so that for example, an extracellular matrix can contain just the basement membrane (or transitional epithelial layer) with the sub-adjacent tunica propria, the tunica submucosa, tunica muscularis, and tunica serosa. The matrix composition can contain any or all of these layers, and thus could conceivably contain only the basement membrane portion, excluding the submucosa, However, generally, and especially since the submucosa is thought to contain and support the active growth factors and other proteins necessary for in vivo tissue regeneration, the matrix composition from any given source will contain the active extracellular matrix portions that support cell development and differentiation and tissue regeneration once placed in a live mammal. This it is generally understood by persons of skill in the art that the extracellular matrix of any of the mammalian tissue consists of several basically inseparable layers broadly termed extracellular matrix. Where layers can be separated these separate layers can electively be included in the composition, depending on whether they serve the purpose that is the goal of the article.

Any incidental extracellular matrix used as part of the composition with the biodegradable polymer can be made as follows. Extracellular matrix can be made into a particulate and fluidized for use in the compositions as described in U.S. Pat. No. 5,275,826 to Badylak, U.S. Pat. No. 6,579,538 to Spievack, and U.S. Pat. No. 6,933,326 to Griffey. Fluidized or emulsified compositions (the liquid or semi-solid forms) can be present at a certain concentration, for example at a concentration of extracellular matrix greater than about 0.001 mg/ml. The concentration of these liquid or semi-solid components of the extracellular matrix composition can be in a range from about 0.001 mg/ml to about 200 mg/ml. The concentrations can further be found in more specific ranges such as for example the following set of ranges: about 5 mg/ml to about 150 mg/ml, about 10 mg/ml to about 125 mg/ml, about 25 mg/ml to about 100 mg/ml, about 20 mg/ml to about 75 mg/ml, about 25 mg/ml to about 60 mg/ml, about 30 mg/ml to about 50 mg/ml, and about 35 mg/ml to about 45 mg/ml, and about 40 mg/ml. to about 42 mg/ml. This set of ranges is exemplary and not intended to be exhaustive. It is contemplated that any value within any of these specifically listed ranges is a reasonable and useful value for a concentration of a liquid or semi-solid component of the composition.

The one or more sheets of extracellular matrix can comprise combinations of forms of extracellular matrix from such sources as, for example but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart extracellular matrix, dermal matrix, and in general extracellular matrix from any mammalian fetal tissue. Any one of these tissue sources can provide extracellular matrix that can then be manipulated into a designated form such as a sandwich or a conduit.

The compositions of the invention that are encased by the sheets of extracellular matrix can be made from a single source of biodegradable polymer, or multiple sources. Some extracellular matrix emulsion or particulate may also be mixed with the biodegradable polymer, although generally, the goal is to have all of the polymer disintegrate or degrade after a suitable period of time in the body.

Depending on the number of sheets in the article or device, the articles or devices can be made from three mammalian tissue sources, four mammalian tissue sources, 5 mammalian tissue sources, 6 mammalian tissue sources, and conceivably up to 10 or more tissue sources. Once again these tissue sources can be from the same mammal (for example the same cow, the same pig, the same rodent, the same human, etc.), the same species of mammal (e.g. a cow, a pig, a rodent, a human), or different mammalian animals (but the same species, e.g. cow 1 and cow 2, or pig 1 and pig 2), or different species of mammals (for example liver matrix from a pig, and small intestine submucosa from a cow, and urinary bladder submucosa from a dog). Any mammal can be a source of the extracellular matrix for these articles, accordingly, humans, cows, pigs, horses, rodents, cats, dogs, and in general any available or suitable mammal can be a source of the required extracellular matrix for these articles.

The articles or devices can be made entirely of one extracellular matrix, for example of small intestine submucosa (SIS) sheets, with biopolymer composition in between some or all of the sheets.

Turning now to the figures, FIG. 1A depicts a sandwich configuration of the article. Element 10 is a bottom sheet of extracellular matrix. Element 8 is a top sheet of extracellular matrix. Element 12 is the composition of biodegradable polymer sandwiched between sheet 8 and 10.

Figure 1B:
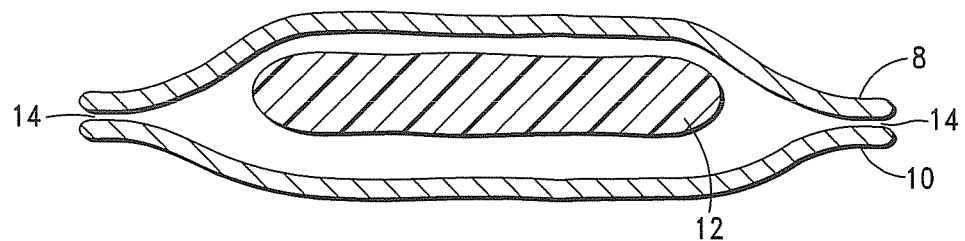
FIG. 1B depicts an article having two sheets of extracellular matrix encasing a composition comprising a biodegradable polymer having the ends of the article closed to fully encase the composition.

FIG. 1B depicts the sandwich with closed ends, the article encasing the composition of biodegradable polymer. Bottom sheet 10 and top sheet 8 are closed or nearly closed at points 14 to encase the biodegradable polymer composition 12.

Figure 1C:
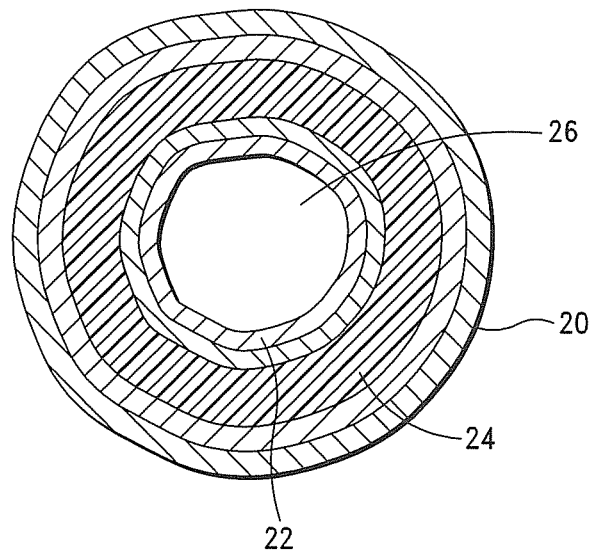
FIG. 1C depicts concentric tubes forming a conduit that encases a biodegradable polymer placed between the two concentric tubes that form the conduit.

FIG. 1C depicts concentric tubes having biopolymer in between them. Outer concentric tube 20 exists on the outside of the article. Composition having biodegradable polymer 24 is between outer tube 20 and inner concentric tube 22. Space 26 exists in the center of the concentric tubes through which fluid or other material can pass after the article is placed in the body at the site where it is needed.

The composition comprising a biodegradable polymer can further include one or more additional components to aid in some aspect of the tissue regenerative process. The additional component will generally be part of the composition comprising biodegradable polymer that is placed between the sheets of matrix. Thus, the additional component can help to regenerate tissue, heal a wound, better recruit stem cells, manipulate the immune environment in a beneficial way, therapeutically treat the local environment, or otherwise contribute to some aspect of the process for which the composition is being used.

Thus, the additional component can be a cell, a protein or a drug (e.g. a small molecule). The cell can be a stem cell, such as, for example a of human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell. This list is not intended to be exhaustive.

The protein can be for example a growth factor, or any other type or protein that might stimulate some part of the tissue regenerative process a collagen, a proteoglycan, a glycosaminoglycan (GAG) chain, a glycoprotein, a growth factor, a cytokine, a cell-surface associated protein, a cell adhesion molecule (CAM), an angiogenic growth factor, an endothelial ligand, a matrikine, a matrix metalloprotease, a cadherin, an immunoglobin, a fibril collagen, a non-fibrillar collagen, a basement membrane collagen, a multiplexin, a small-leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, nuerocan, brevican, cytoplasmic domain-44 (CD44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF). This list is not intended to be exhaustive.

The additional component can also be a drug, such as an agent that has therapeutic properties. The drug can be bioactive and play some role in the process of tissue regeneration, for example, or act as an antibiotic, antiviral, or other active therapeutic agent serving a purpose in the composition as a whole, also by example. The drug can be a small molecule, or any other agent having therapeutic properties. The drug can have the capacity to treat the patient locally at the site of placement of the article, as for example a local antibiotic or anti-inflammatory agent. The drug may also alternatively have the capacity to treat the patient or subject systemically, as with a molecule that can travel in the blood stream from the site of placement of the article to other parts of the body where it can have effects, e.g. a therapeutic agent that can have effects in another system in the patient.

The invention contemplates using the articles for regenerating tissue as a defect or healing a wound in mammalian tissue. The defect can be a cut, disease, wound, burn, scar, necrosis, or other abnormality that would be beneficial to the patient to treat. Regenerating tissue at the defect can be one response elicited from the step of placing the extracellular matrix sheets in contact with the defect, while the biodegradable polymer can help hold a shape or support the extracellular matrix sheet until the tissue regenerates or the wound heals. If the defect is a wound in need of healing, wound healing may be another response that occurs as a result of placing the extracellular matrix at the wound site. In general any term that identifies that the tissue could benefit from healing or where the concept of tissue regeneration fits within the scope of the use for the composition can be used to describe the process that is the goal of placing the article in the patient.

Therapeutically effective amount is a term meant to capture the idea that you need to apply enough of an element of the composition in sufficient strength so that the composition can have a positive effect on the tissue that is being treated in the subject. Thus, the term therapeutically effective amount applies to the additional components added to the composition comprising the biodegradable polymer. The term therapeutically effective amount may therefore apply to a quantity of matrix, or a size of a sheet of matrix, or a volume or weight of powder, or a concentration of liquid or emulsion. That the amount is therapeutically effective is determined by the composition's ability to have a regenerative or wound healing effect at the site where the composition contacts the tissue. A therapeutically effective amount is determinable by routine testing in patients with wounds or defects. In general a minimal therapeutically effective amount would be considered sufficient composition to contact amply all of the wound or defect in the tissue.

Regenerating tissue is the ability to make tissue regrow, an organ regrow itself, and for new tissue to reform without scarring. Healing a wound is the ability of the tissue to heal without scarring, or with less scarring than would have occurred without the article.

All references cited are incorporated in their entirety. Although the foregoing invention has been described in detail for purposes of clarity of understanding, it will be obvious that certain modifications may be practiced within the scope of the appended claims.

What is claimed is:

1. A method for regenerating mammalian tissue, comprising the steps of:
    identifying a defective tissue site in a mammalian structure;
    providing a tissue regeneration member comprising an outer tube member, a concentric inner tube member and a biodegradable polymeric emulsion disposed between said outer tube member and said concentric inner tube member,
    said concentric inner tube comprising a lumen therethrough that is configured to allow fluid flow therethrough,
    said outer tube member comprising first decellularized extracellular matrix (ECM) derived from mammalian liver basement membrane tissue,
    said concentric inner tube member comprising second decellularized ECM derived from small intestine submucosa tissue,
    said biodegradable polymeric emulsion comprising poly ε-caprolactone and an antibiotic; and
    contacting said defective tissue site with said tissue regeneration member, wherein new tissue is regenerated at said defective tissue site.

2. The method of claim 1, wherein said biodegradable polymeric emulsion further comprises a growth factor selected from the group consisting of transforming growth factor beta (TGF-β), fibroblast growth factor-2 (FGF-2) and vascular epithelial growth factor (VEGF).

* * * * *